United States Patent [19]

Schlecker et al.

[11] Patent Number: 4,845,096

[45] Date of Patent: Jul. 4, 1989

[54] BENZOFURAN DERIVATIVES AND ANTIULCEROGENIC AGENTS CONTAINING SAME

[75] Inventors: Rainer Schlecker, Bissersheim; Klaus Ruebsamen, Neustadt, both of Fed. Rep. of Germany

[73] Assignee: BASF Aktiengesellschaft, Ludwigshafen, Fed. Rep. of Germany

[21] Appl. No.: 170,321

[22] Filed: Mar. 18, 1988

[30] Foreign Application Priority Data

Mar. 30, 1987 [DE] Fed. Rep. of Germany ....... 3710469

[51] Int. Cl.[4] .................. A61K 31/445; C07D 405/14
[52] U.S. Cl. .................. 514/233.5; 514/255; 514/269; 514/318; 514/320; 514/378; 514/406; 514/422; 514/444; 514/469; 544/122; 544/124; 544/131; 544/137; 544/140; 544/141; 544/146; 544/153; 544/295; 544/333; 544/360; 544/367; 544/371; 544/372; 544/379; 546/194; 546/196; 546/269; 548/247; 548/374; 548/518; 548/525; 549/60; 549/471
[58] Field of Search .............. 544/140, 333, 360, 122, 124, 131, 146, 152, 295, 367, 379, 137, 141, 544/372, 371; 546/194, 196, 269; 548/247, 336, 374, 518, 525; 549/60, 471; 514/255, 239, 318, 320, 230, 269, 378, 406, 422, 444, 469, 233.5

[56] References Cited

U.S. PATENT DOCUMENTS

| | | | |
|---|---|---|---|
| 3,631,034 | 12/1971 | Fauran et al. | 549/471 |
| 3,658,822 | 4/1972 | Fauran et al. | 544/370 |
| 3,850,937 | 12/1974 | Fauran et al. | 549/471 |
| 3,862,176 | 1/1975 | Fauran et al. | 549/471 |
| 4,153,620 | 5/1970 | Bourgery et al. | 544/368 |

FOREIGN PATENT DOCUMENTS

| | | |
|---|---|---|
| 1933178 | 1/1970 | Fed. Rep. of Germany . |
| 2238115 | 3/1973 | Fed. Rep. of Germany . |
| 2730593 | 1/1978 | Fed. Rep. of Germany . |

OTHER PUBLICATIONS

Chemical Abstract (1974) 81(17):99 240k.
Chemical Abstract (1974) 81(9):45196g.
European Journal of Medicinal Chemistry—Chimica Therapeutica—EDIFOR Pub. Office, Paris, vol. 9 (1974) pp. 85-93.

Primary Examiner—Richard A. Schwartz
Assistant Examiner—Bernard J. Dentz
Attorney, Agent, or Firm—Keil & Weinkauf

[57] ABSTRACT

Benzofuran derivatives of the general formula I

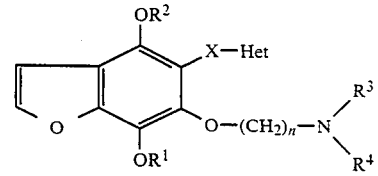

where $R^1$ and $R^2$ are each hydrogen, alkyl or phenylalkyl, where alkyl in each case is of 1 to 4 carbon atoms, $R^3$ and $R^4$ are identical or different and are each hydrogen or $C_1$-$C_4$-alkyl or together form a 3-membered to 5-membered chain which may be interrupted by an oxygen atom or an $NR^1$ group, X is —CO—CH=CH—, —CO—CH$_2$—CH$_2$—or —CHOH—CH$_2$—CH$_2$—, n is 2 or 3 and Het is an aromatic 5-membered or 6-membered ring which contains a hetero atom from the group consisting of N, O and S and may additionally contain a (further) N atom, in which the ring may be substituted by $C_1$-$C_4$-alkyl, fluorine, chlorine, bromine, $NH_2$ or $NR^1R^2$, where $R^1$ and $R^2$ have the abovementioned meanings, the use of these benzofuran derivatives for the preparation of pharmaceutical, in particular antiulcerogenic, agents, and these agents themselves are described.

4 Claims, No Drawings

BENZOFURAN DERIVATIVES AND ANTIULCEROGENIC AGENTS CONTAINING SAME

The present invention relates to novel benzofuran derivatives of the general formula I and therapeutic agents containing these derivatives.

DE-A-No. 22 35 941 mentions eleven different pharmacological actions, including antiulcerous properties, for benzofuran derivatives of the general formula I where an unsubstituted or substituted phenyl radical is present instead of Het. However, these properties are relatively weak. Following on logically from this, the subsequent report from the same laboratory by G. Raynaud et al. in Eur. J. Med. Chem.—Chimica Therapeutica, Edifor-Verl., Paris, 9 (1974), 85 describes seven different types of properties for this class of substances but does not mention an antiulcerous action. The compounds also possess undesirable Ca-antagonistic activity.

We have found, surprisingly, that compounds of the general formula I

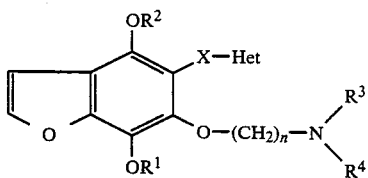

in which the phenyl ring of the piprofurol is replaced by a heterocycle has only a very weak Ca-antagonistic action but powerful antiulcerogenic activity, in contrast to the known compounds of similar structure.

In the general formula I, $R^1$ and $R^2$ are each hydrogen, alkyl or phenylalkyl, where alkyl in each case is of 1 to 4 carbon atoms, $R^3$ and $R^4$ are identical or different and are each hydrogen or $C_1$-$C_4$-alkyl or together form a 3-membered to 5-membered chain which may be interrupted by an oxygen atom or a $NR^1$ group, X is —CO—CH=CH—, —CO—CH$_2$—CH$_2$— or —CHOH—CH$_2$—CH$_2$—, n is 2 or 3 and Het is an aromatic 5-membered or 6-membered ring which contains a hetero atom from the group consisting of N, O and S and may additionally contain a (further) N atom, or an aromatic 6-membered ring which contains 1 or 2 N atoms, in which the ring may be substituted by $C_1$-$C_4$-alkyl, fluorine, chlorine, bromine, $NH_2$ or $NR^1R^2$, where $R^1$ and $R^2$ have the abovementioned meanings.

Examples of heterocycles are pyrazole, pyrrole, thiophene, furan, isoxazole, pyridine or pyrimidine.

The compounds of the general formula I where X is —CO—CH$_2$—CH$_2$— can be prepared from the compounds of the formula I in which X is —CO—CH=CH— by catalytic hydrogenation of the double bond by a method known from the literature, as described in, for example, R. N. Rylander, "Catalytic Hydrogenation over Pt Metals", Acad. Press, New York, page 282, 1967. Particularly suitable catalysts are metal catalysts, such as palladium on carbon or Raney nickel in alcohol.

The compounds of the general formula I in which X is —CH(OH)—CH$_2$—CH$_2$— can be prepared by reduction of the compounds of the general formula I where X is —CO—CH$_2$—CH$_2$— with a metal hydride by a conventional method, as described in Houben-Weyl, Methoden der org. Chemie. 4th Edition, G. Thieme Verlag Stuttgart 1984, Volume 6/1 b, page 145. Examples of suitable metal hydrides are LiAlH$_4$ in an ether or NaBH$_4$ in an alcohol, such as ethanol or isopropanol.

These compounds can also be prepared from the compounds of the formula I where X is —CO—CH=CH— by catalytic hydrogenation, as described in Houben-Weyl Vol. 6/1 b, page 61, or by reduction with a metal hydride, as described in Houben-Weyl, 4th Edition (1981), Vol. 4/1 d, page 297 and in German Laid-Open Application DOS No. 2,235,941.

Compounds of the formula I where X is CO—CH=CH$_2$ are synthesized from the acetophenones of the formula II by condensation with aromatic heterocyclic aldehydes by a conventional method, as described in, for example, Org. Reactions Vol. 16, page 1 et seq., John Wiley, New York 1968. Examples of suitable condensing agents are alkali metal hydroxides in aqueous alcoholic solution.

Some of the compounds of the formula II where $R^1$ and $R^2$ are each $CH_3$ are known and can be obtained by alkylation of the o-hydroxyacetophenone khellinone X (J. Amer. Chem. Soc. 72 (1950), 1613) with a haloalkylamine, as described in Chimie Therapeutique 4 (1973), 475. The alkylation of X

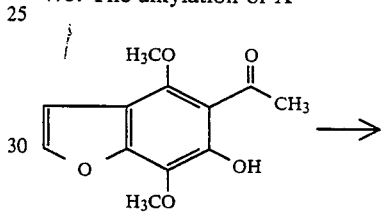

X

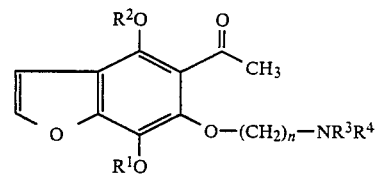

II can also be carried out with an aminoalcohol under the conditions of the Mitsunobu method (Synth. 1981, 1).

The compounds of the formula II in which $R^1$ or $R^2$ is not $CH_3$ can be prepared by alkylation of the hydroxyacetophenones III

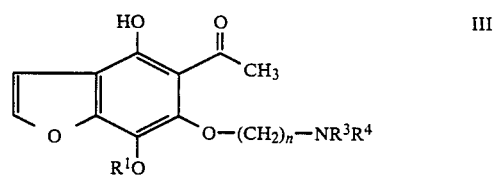

by a conventional method for phenol synthesis (Houben-Weyl Vol. VI/3, page 49 et seq.). For example, the alkylation can be carried out with an alkyl halide, using an alkali metal carbonate as a base in acetone as a solvent or a metal hydride in an aprotic solvent, such as dimethylformamide or tetrahydrofuran.

The compounds III are obtainable by hydrogenolysis of the benzyl ether IV by a known method (Houben-Weyl, Vol. 4/1c, page 385 et seq.). The debenzylation is preferably carried out at room temperature in order to avoid hydrogenation of the furan ring.

The compounds IV are synthesized from the hydroxyacetophenones V by the methods described for the preparation of II (where $R^1$ and $R^2$ are each $CH_3$).

The hydroxyacetophenone V is prepared by ring cleavage of the pyrone VI under alkaline conditions by a conventional method, as described for the hydrolysis of khellin in J. Amer. Chem. Soc. 73 (1950), 1613.

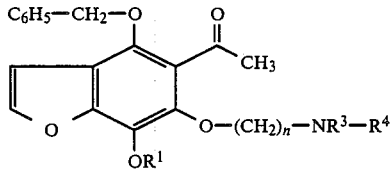

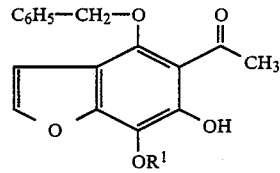

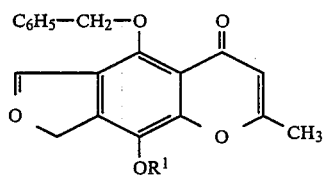

The compound VI is obtained by benzylation of the phenol VII by generally known methods, as described for the synthesis of II ($R^1$ or $R^2$ is $CH_3$).

The phenol VII where $R^1$ is $CH_3$ can be synthesized by a method known from the literature (Liebigs Ann. 704 (1967), 182) by selective ether cleavage of khellin with KI/formic acid.

The phenol VII where $R^1$ is not $CH_3$ can be prepared by selective alkylation of khellinquinol VIII, as described in Ann. Pharm. Fr. 11 (1953), 685.

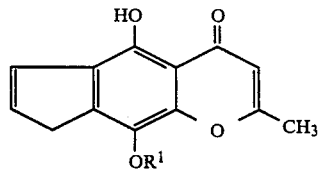

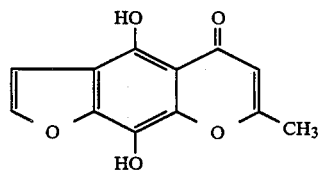

The novel compounds of the formula I in which X is $CHOH-CH_2-CH_2-$ possess a center of chirality and are obtained as racemates which can be resolved into the optically active antipodes by known methods, for example by forming diastereomeric salts with optically active auxiliary acids or dibenzoyltartaric acid, camphor-10-sulfonic acid or ditolyltartaric acid.

If necessary, the resulting compounds according to the invention are converted into the addition salt of a physiologically tolerated acid. A summary of conventional physiologically tolerated acids is given in Fortschritte der Arzneimittelforschung 1966, Birkhauser Verlag, Vol. 10, pages 224–285, Germany, Switzerland.

The addition salts with acids are as a rule obtained in a conventional manner by mixing the free base or a solution thereof with the appropriate acid or a solution thereof in an organic solvent, for example a lower alcohol, such as methanol, ethanol or propanol, or a lower ketone, such as acetone, methyl ethyl ketone or methyl isobutyl ketone, or an ether, such as diethyl ether, tetrahydrofuran or dioxane. To achieve better crystallization, it is also possible to use mixtures of the stated solvents. Furthermore, pharmaceutically acceptable aqueous solutions of acid addition compounds of the aminopropanol derivatives of the formula I can be prepared by dissolving the free bases in an aqueous acid solution.

The novel compounds and their physiologically tolerated addition salts with acids possess antiulcerous and secretion-inhibiting properties and are therefore particularly suitable for the treatment of gastric disorders.

The present invention accordingly also relates to therapeutic agents or formulations which, in addition to conventional pharmaceutical carriers and diluents, contain a compound of the formula I or one of its physiologically tolerated addition salts with acids as an active compound, and the use of the novel compounds for therapeutic purposes.

The therapeutic agents and formulations are prepared in a known manner using the conventional carriers or diluents and the pharmaceutical auxiliaries usually employed, in accordance with the desired route of administration and with a suitable dose (cf. R. Voigt, Lehrbuch der pharmazeutischen Technologie, VEB-Verlag Volk und Gesundheit, Berlin 1975). Suitable single therapeutic doses are from 1 to 500, preferably from 5 to 100, mg.

The preferred formulations consist of an administration form which is suitable for oral administration. Such administration forms are tablets, film tablets, coated tablets, capsules, pills, powders, solutions or suspensions or depot forms.

Of course, parenteral formulations, such as injection solutions, are also suitable. Other examples of formulations are suppositories. For use in practice, the compounds to be used according to the invention are mixed with the conventional pharmaceutical carriers. The appropriate tablets can be obtained, for example, using inert diluents, such as dextrose, sucrose, sorbitol, polyvinylpyrrolidone, mannitol, calcium carbonate, calcium phosphates or lactose, disintegrating agents, such as corn starch, alginic acid or polyvinylpyrrolidone, binders such as starch or gelatine, lubricants, such as magnesium stearate or talc, and/or agents for achieving a depot effect, such as cellulose acetate phthalate or polyvinyl acetate. The tablets can also consist of a plurality of layers.

Correspondingly, coated tablets can be prepared by coating cores, prepared similarly to the tablets, with agents conventionally used in tablet coatings, for example polyvinylpyrrolidone or shellac, gum arabic, talc, titanium dioxide or sugar. The tablet coating can also consist of a plurality of layers, and the auxiliaries mentioned above in connection with the tablets may be used therein.

Solutions or suspensions containing the novel active compounds may additionally contain flavor improvers, such as saccharine, cyclamate or sugar, and, for example, aromas, such as vanillin or orange extract. They may also contain suspending agents, such as sodium carboxymethylcellulose, or preservatives, such as p-hydroxybenzoates. Capsules containing active compounds can be prepared, for example, by mixing the active compound with an inert carrier, such as lactose or sorbitol, and encapsulating the mixture in gelatin capsules.

Suitable suppositories can be prepared, for example, by mixing with carriers intended for this purpose, such as neutral fats or polyethylene glycol or their derivatives, and shaping the mixture.

A. Preparation of starting compounds

4-Benzyloxy-9-methoxy-7-methylfuro[3,2-g]chromone
(VI where $R^2$ is $CH_3$)

95 g of 4-hydroxy-9-methoxy-7-methylfuro[3.2-g]chromone in 1,000 ml of methyl ethyl ketone are refluxed with 100 g of benzyl bromide and 210 g of $K_2CO_3$ for 15 hours. 1,000 ml of $CH_2Cl_2$ are added to the mixture, which is then filtered, and the solvent is distilled off. After treatment with petroleum ether, the residue gives 123 g of VI (where $R^1$ is $CH_3$) as a yellowish oil.

5-Acetyl-4-benzyloxy-6-hydroxy-7-methoxybenzofuran
(V where $R^1$ is $CH_3$)

113 g of VI (where $R^1$ is $CH_3$) are added a little at a time to a solution of 67 g of KOH in 1,000 ml of water at 75° C. The mixture is refluxed for 3 hours, cooled and filtered. The filtrate is acidified with 110 ml of concentrated hydrochloric acid, and the precipitated residue is filtered off under suction and dried. 115 g of V (where $R^1$ is $CH_3$) are obtained.

5-Acetyl-4-benzyloxy-7-methoxy-6-(2-N-piperidinoethoxy)benzofuran (general formula IV)

50 g of V (where $R^1$ is $CH_3$) in 400 ml of methyl ethyl ketone are refluxed with 35 g of chloroethyl-piperidine/90 g of $K_2CO_3$ for 5 hours. The mixture is filtered, the filtrate is evaporated down and the residue is partitioned between water and ether. 69 g of IV (where $R^1$ is $CH_3$) are obtained as a yellowish oil.

5-Acetyl-4-hydroxy-7-methoxy-6-(2-N-piperidinoethoxy)benzofuran (general formula III)

18.5 g of IV (where $R^1$ is $CH_3$ and $R^3$ and $R^4$ together form pentamethylene) are dissolved in 150 ml of ethyl acetate and the solution is stirred in a hydrogenation apparatus with 1 g of Pd/C under atmospheric pressure and at room temperature until the absorption of hydrogen is complete. The catalyst is filtered off and the filtrate is evaporated down. The residue gives 16 g of the desired product.

5-Acetyl-4-ethoxy-7-methoxy-6-(2-piperidinoethoxy)-benzofuran

5-Acetyl-4-hydroxy-7-methoxy-7-(2-piperidinoethoxy)-benzofuran in 2 ml of dimethylformamide are added dropwise, at room temperature, to a suspension of 0.4 g of NaH (55% strength in liquid paraffin) in 10 ml of dimethylformamide. The mixture is stirred for 30 minutes, after which 2.1 g of ethyl iodide are added. Stirring is continued overnight and the mixture is poured onto ice and extracted with ether. The ether phase is washed with water and evaporated down, and the residue is partitioned between $CH_2Cl_2$ and 1N HCl. The organic phase is dried and evaporated down. 2.0 g of the hydrochloride of the desired compound are obtained.

Examples of compounds prepared in a similar manner are:

5-acetyl-4-propoxy-7-methoxy-6-(2-piperidinoethoxy)-benzofuran; oil 5-acetyl-4,7-diethoxy-6-(2-piperidinoethoxy)-benzofuran; oil 5-acetyl-4-ethoxy-7-methoxy-6-(3-piperidinopropoxy)-benzofuran; oil 5-acetyl-4-ethoxy-7-methoxy-6-(2-morpholinoethoxy)-benzofuran; oil 5-acetyl-4-ethoxy-7-methoxy-6-(2-dimethylaminoethoxy)benzofuran; oil 5-acetyl-4-ethoxy-7-methoxy-6-(2-pyrrolidinoethoxy)-benzofuran; oil 5-acetyl-4-ethoxy-7-methoxy-6-(2-(4-methyl-piperazino)ethoxy)-benzofuran; oil Examples of the preparation of the compounds according to the invention.

EXAMPLE 1

1-[4,7-dimethoxy-6-(2-piperidinoethoxy)-benzofuran-5-yl]-3-(1-methylpyrazol-4-yl)-propenone A solution of 11 g of NaOH in 11 ml of water was added to 8.0 g of 5-acetyl-4,7-dimethoxy-6-(2-piperidinoethoxy)-benzofuran and 2.6 g of 1-methyl-pyrazole-4-aldehyde in 60 ml of ethanol. The mixture was stirred overnight, poured over water and extracted with $CH_2Cl_2$. The solvent was stripped off to give 9.0 g of a yellowish oil. The latter was dissolved in methyl tert-butyl ether and precipitated as the hydrochloride by adding hydrochloric acid in ether. Yield 8.5 g, mp. 78°–80° C.

The Examples in Table 1 were synthesized in a similar manner. The structures of all compounds were confirmed by NMR spectroscopy.

EXAMPLE 22

1-(4-Ethoxy-7-methoxy-6-(2-piperidinoethoxy)-benzofuran-5-yl)-3-(1-methylpyrazol-4-yl)-propanone 6.6 g of 1-(4-ethoxy-7-methoxy-6-(2-piperidinoethoxy)-benzofuran-5-yl)-3-(1-methylpyrazol-4-yl)-propenone in 200 ml of methanol were hydrogenated with 0.8 g of Pd/C (10%) under atmospheric pressure until the calculated amount of hydrogen had been absorbed. The catalyst was filtered off, the filtrate was evaporated down and the residue was chromatographed (1:1 $CH_2Cl_2$/methanol).

Yield: 3.3 g (oil).

The following were prepared in a similar manner:

EXAMPLE 23

1-(4-Ethoxy-7-methoxy-6-(2-piperidinoethoxy)-benzofuran-5-yl)-3-(1-ethylpyrazol-4-yl)-propanone. The substance was obtained as an oil

EXAMPLE 24

1-(4-Ethoxy-7-methoxy-6-(2-piperidinoethoxy)-benzofuran-5-yl)-3-(thien-3-yl)-propanone The substance was obtained as an oil.

EXAMPLE 25

1-(4-Ethoxy-7-methoxy-b 6-(2-piperidinoethoxy)-benzofuran-5-yl)-3-(thien-3-yl)-propanol 9 g of 1-(4-ethoxy-7-methoxy-6-(2-piperidinoethoxy)-benzofuran-5-yl)-3-(thien-3-yl)-propanone in 30 ml of isopropanol were refluxed with 3.3 g of NaBH$_4$ for 6 hours. The mixture was poured onto ice water and extracted with CH$_2$Cl$_2$. The organic phase was dried, the solvent was distilled off and the residue was treated with petroleum ether and then dissolved in ether. The addition of equivalent amounts of HCl in ether gave 1.3 g of the product as the hydrochloride. Mp. 138°–139° C.

EXAMPLE 26

1-(4-Ethoxy-7-methoxy-6-(2-piperidinoethoxy)-benzofuran-5-yl)-3-(1-methylpyrrol-3-yl)-propanol 3.4 g of NaBH$_4$ and a few drops of concentrated NaOH were added to 9.7 g of propenone from Example 6 in 30 ml of isopropanol/7 ml of pyridine, and refluxing was carried out for 10 hours. The mixture was evaporated down in a rotary evaporator, the residue was partitioned between CH$_2$Cl$_2$ and water, the organic phase was separated off and dried with Na$_2$SO$_4$, and the solvent was stripped off. Digestion with petroleum ether gave 2.5 g of product. Mp. 88° C.

The compounds of Table 2 were prepared in a similar manner.

TABLE 1

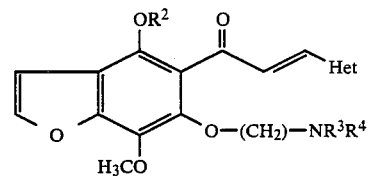

| Example no. | R$^1$ | R$^2$ | n | NR$^3$R$^4$ | Het | mp. [°C.] |
|---|---|---|---|---|---|---|
| 2 | CH$_3$ | CH$_3$ | 2 | piperidine | 1-methylpyrrol-2-yl | 115–117 (Oxalate) |
| 3 | CH$_3$ | CH$_3$ | 2 | piperidine | thien-2-yl | 126–127 (Oxalate) |
| 4 | CH$_3$ | CH$_3$ | 2 | piperidine | 2-methylthien-5-yl | 118–120 (Oxalate) |
| 5 | CH$_3$ | CH$_3$ | 2 | piperidine | pyridyl | 112–114 (Oxalate) |
| 6 | CH$_3$ | C$_2$H$_5$ | 2 | piperidine | 1-methylpyrrol-3-yl | oil |
| 7 | CH$_3$ | C$_2$H$_5$ | 2 | piperidine | 1-ethylpyrazol-3-yl | 42 (Oxalate) |
| 8 | CH$_3$ | C$_2$H$_5$ | 2 | piperidine | 1-methylpyrazol-4-yl | oil |

TABLE 1-continued

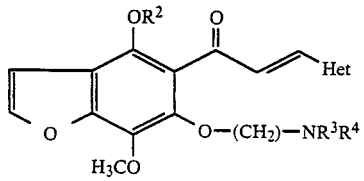

| Example no. | R¹ | R² | n | NR³R⁴ | Het | mp. [°C.] |
|---|---|---|---|---|---|---|
| 9 | CH₃ | C₆H₅—CH₂ | 2 |  piperidine | 1-methylpyrazole | oil |
| 10 | CH₃ | C₂H₅ | 2 | piperidine | thiophene | oil |
| 11 | CH₃ | C₃H₇ | 2 | piperidine | 1-methylpyrazole | oil |
| 12 | CH₃ | C₂H₅ | 2 | piperidine | 1-methylpyrazole | oil |
| 13 | CH₃ | C₂H₅ | 2 | piperidine | 3-methylisoxazole | oil |
| 14 | CH₃ | C₂H₅ | 2 | piperidine | pyridine | oil |
| 15 | CH₃ | C₂H₅ | 2 | piperidine | pyridine | oil |
| 16 | CH₃ | C₂H₅ | 2 | morpholine | 1-methylpyrazole | oil |
| 17 | CH₃ | C₂H₅ | 2 | piperidine | 1-methylpyrazole | oil |
| 18 | CH₃ | C₂H₅ | 3 | piperidine | 1-methylpyrazole | oil |

TABLE 1-continued

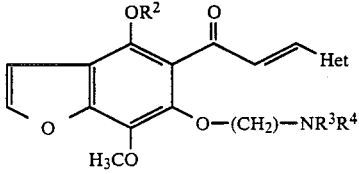

| Example no. | R¹ | R² | n | NR³R⁴ | Het | mp. [°C.] |
|---|---|---|---|---|---|---|
| 19 | CH₃ | C₂H₅ | 2 | piperidine | pyrimidine-N(CH₃)₂ | 143–144 |
| 20 | CH₃ | C₂H₅ | 2 | N-methylpiperazine | 1-methylpyrazole | oil |
| 21 | CH₃ | C₂H₅ | 2 | piperidine | 1-methylpyrazole | oil |

TABLE 2

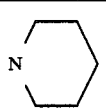

| Example no. | R¹ | R² | n | NR³R⁴ | Het | mp. [°C.] |
|---|---|---|---|---|---|---|
| 27 | CH₃ | CH₃ | 2 | piperidine | N-methylpyrrole | 57–58 (Oxalate) |
| 28 | CH₃ | CH₃ | 2 | piperidine | 1-methylpyrazole | 46 (Oxalate) |
| 29 | CH₃ | CH₃ | 2 | piperidine | thiophene | 43 (Oxalate) |
| 30 | CH₃ | CH₃ | 2 | piperidine | thiophene | 58 (Oxalate) |
| 31 | CH₃ | C₂H₅ | 2 | piperidine | 1-methylpyrazole | oil |

TABLE 2-continued

Structure: benzofuran with OR² (top), OH-CH(CH₂CH₂-Het), OR¹ (bottom), and O-(CH₂)ₙ-NR³R⁴ substituents.

| Example no. | R¹ | R² | n | NR³R⁴ | Het | mp. [°C.] |
|---|---|---|---|---|---|---|
| 32 | CH₃ | C₂H₅ | 2 | piperidinyl | 1-ethyl-4-methylpyrazol-yl | 88 |
| 33 | CH₃ | C₆H₅CH₂ | 2 | piperidinyl | 1,4-dimethylpyrazol-yl | 53 |
| 34 | CH₃ | C₃H₇ | 2 | piperidinyl | 1,4-dimethylpyrazol-yl | oil |
| 35 | CH₃ | C₂H₅ | 2 | piperidinyl | 1,3-dimethylpyrazol-yl | 64 |
| 36 | CH₃ | C₂H₅ | 2 | piperidinyl | 3,5-dimethylisoxazol-yl | oil |
| 37 | CH₃ | C₂H₅ | 2 | piperidinyl | pyridin-4-yl | 72 (Oxalate) |
| 38 | CH₃ | C₂H₅ | 2 | piperidinyl | pyridin-3-yl | 133 (Oxalate) |
| 39 | CH₃ | C₂H₅ | 2 | piperidinyl | 4-methylimidazol-yl | oil |
| 40 | CH₃ | C₂H₅ | 2 | morpholinyl | 1,4-dimethylpyrazol-yl | oil |
| 41 | CH₃ | C₂H₅ | 2 | piperidinyl | 1,2-dimethylimidazol-yl | oil |

TABLE 2-continued

Structure: Benzofuran with OR² at position 4, OH on side chain $-CH(OH)-CH_2-CH_2-Het$, OR¹ at position 7, and $O-(CH_2)_n-NR^3R^4$ substituent.

| Example no. | R¹ | R² | n | NR³R⁴ | Het | mp. [°C.] |
|---|---|---|---|---|---|---|
| 42 | CH₃ | C₂H₅ | 3 | piperidinyl | 1-methyl-pyrazol-4-yl | oil |
| 43 | CH₃ | C₂H₅ | 2 | piperidinyl | 2-(dimethylamino)-pyrimidin-5-yl | oil |
| 44 | CH₃ | C₂H₅ | 2 | piperidinyl | 1,5-dimethyl-imidazol-4-yl | 98 |
| 45 | CH₃ | C₂H₅ | 2 | 4-methyl-piperazin-1-yl | 1-methyl-pyrazol-4-yl | oil |
| 46 | C₂H₅ | C₂H₅ | 2 | piperidinyl | 1-methyl-pyrazol-4-yl | oil |
| 47 | CH₃ | C₂H₅ | 2 | pyrrolidinyl | 1-methyl-pyrazol-4-yl | oil |
| 48 | CH₃ | C₂H₅ | 2 | —N(CH₃)₂ | 1-methyl-pyrazol-4-yl | oil |
| 49 | CH₃ | CH₂ | 2 | pyrrolidinyl | 1-methyl-pyrazol-4-yl | oil |

We claim:
1. A benzofuran derivative of the formula I

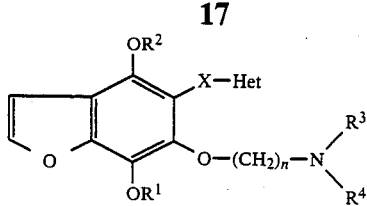

where $R^1$ and $R^2$ are each hydrogen, alkyl or phenylalkyl, where alkyl in each case is of 1 to 4 carbon atoms, $R^3$ and $R^4$ are identical or different and are each hydrogen or $C_1$-$C_4$-alkyl or together form a 3-membered to 5-membered chain which may be interrupted by an oxygen atom or an $NR^1$ group, X is —CO—CH=CH—, —CO—CH$_2$—CH$_2$— or —CHOH—CH$_2$—CH$_2$, n is 2 or 3 and Het is a member selected from the group consisting of pyrazole, pyrrole, thiophene, furan, isoxazole, pyridine and pyrimidine, which member may be substituted by $C_1$-$C_4$-alkyl, fluorine, chlorine, bromine, $NH_2$ or $NR^1R^2$, where $R^1$ and $R^2$ have the abovementioned meanings and, physiologically tolerated acid addition salts thereof.

2. A compound of the formula I as defined in claim 1 or a salt thereof, wherein $R^3$ and $R^4$ with the nitrogen atom to which they are attached form a piperidino, morpholino, pyrrolidino, or 4-methylpiperizino group.

3. An antiulcerogenic composition which comprises:
a pharmaceutical carrier and as an active agent, an effective amount of a compound of the formula I or a salt thereof as defined in claim 1.

4. A process for treating gastric disorders which comprises administering to a patient in need thereof an effective amount of a composition as defined in claim 3.

* * * * *